United States Patent
Bechtold et al.

(10) Patent No.: US 6,954,666 B2
(45) Date of Patent: Oct. 11, 2005

(54) METHOD FOR LOCAL REDUCTION OF THE OPERATING NOISE PRODUCED BY A MEDICAL DIAGNOSTIC OR THERAPY DEVICE, AND MEDICAL DIAGNOSTIC OR THERAPY DEVICE HAVING A DEVICE FOR IMPLEMENTING SUCH A METHOD

(75) Inventors: Mario Bechtold, Hemhofen (DE); Ralph Oppelt, Uttenreuth (DE)

(73) Assignee: Siemens Aktiengesellschaft, Munich (DE)

( * ) Notice: Subject to any disclaimer, the term of this patent is extended or adjusted under 35 U.S.C. 154(b) by 157 days.

(21) Appl. No.: 10/414,500

(22) Filed: Apr. 16, 2003

(65) Prior Publication Data

US 2003/0212328 A1 Nov. 13, 2003

(30) Foreign Application Priority Data

Apr. 16, 2002 (DE) .......................... 102 16 859

(51) Int. Cl.[7] .............................. A61B 5/05
(52) U.S. Cl. .................................... 600/410
(58) Field of Search ............ 600/407, 409–410, 600/437, 439; 181/30, 175; 381/71.1, 71.6, 71.9, 71.14

(56) References Cited

U.S. PATENT DOCUMENTS

| | | | | |
|---|---|---|---|---|
| 4,823,908 A | * | 4/1989 | Tanaka et al. ............... | 181/175 |
| 5,022,082 A | * | 6/1991 | Eriksson et al. ............ | 381/71.8 |
| 5,033,082 A | * | 7/1991 | Eriksson et al. ........ | 379/406.08 |
| 5,133,017 A | * | 7/1992 | Cain et al. .................. | 381/71.6 |
| 5,313,945 A | * | 5/1994 | Friedlander ................. | 600/410 |
| 5,357,578 A | * | 10/1994 | Taniishi ....................... | 381/354 |
| 5,427,102 A | * | 6/1995 | Shimode et al. ............ | 600/410 |
| 5,577,504 A | * | 11/1996 | Salloway et al. ........... | 600/410 |
| 6,011,855 A | * | 1/2000 | Selfridge et al. ........... | 381/111 |
| 6,179,792 B1 | * | 1/2001 | Krause .......................... | 601/2 |
| 6,421,649 B1 | * | 7/2002 | Rattner .......................... | 705/2 |
| 6,434,239 B1 | * | 8/2002 | DeLuca ..................... | 381/71.2 |
| 6,463,316 B1 | * | 10/2002 | Brungart ..................... | 600/410 |
| 6,577,738 B2 | * | 6/2003 | Norris et al. ................. | 381/77 |

FOREIGN PATENT DOCUMENTS

| EP | 0597528 A1 | 5/1994 |
|---|---|---|
| GB | 2281970 A | 3/1995 |

OTHER PUBLICATIONS

Technology Licensing–HyperSonic Sound, American Technology Corporation, Internet Document: http://www.atcsd.com/tl–hss.html, printed on Jan. 15, 2002.

* cited by examiner

*Primary Examiner*—Francis J. Jaworski
(74) *Attorney, Agent, or Firm*—Staas & Halsey LLP

(57) ABSTRACT

In a method for local reduction of the operating noise produced by a medical diagnostic or therapy device, antisound is produced locally by a sound source. The sound source used is a highly directional parametric loudspeaker. As a result, disturbing operating noises can be limited locally and suppressed effectively.

21 Claims, 1 Drawing Sheet

METHOD FOR LOCAL REDUCTION OF THE OPERATING NOISE PRODUCED BY A MEDICAL DIAGNOSTIC OR THERAPY DEVICE, AND MEDICAL DIAGNOSTIC OR THERAPY DEVICE HAVING A DEVICE FOR IMPLEMENTING SUCH A METHOD

CROSS REFERENCE TO RELATED APPLICATIONS

This application is based on and hereby claims priority to German Application No. 102 16 859.8 filed on Apr. 16, 2002, the contents of which are hereby incorporated by reference.

BACKGROUND OF THE INVENTION

One aspect of the invention relates to a method for local reduction of the operating noise produced by a medical diagnostic or therapy device, and medical diagnostic or therapy device having a device for implementing such a method.

Medical diagnostic or therapy devices, for example magnetic resonance tomographs or lithotripters, produce disturbing operating noise, to which the patient to be examined or treated is primarily exposed. High levels of noise occur for the patient, in particular in magnetic resonance tomographs, and, inside the magnet, can reach up to 120 dB(A) there. Such a noise level constitutes an enormous burden on the patient, both psychologically and physically, in particular under the restricted space conditions within a magnetic resonance tomograph. In order to reduce this burden, it is known to use, firstly, passive ear protection measures, for example earplugs or earmuffs, or, secondly, by constructive measures on the diagnostic and therapy device itself, to reduce its operating noise. Both measures are effective only up to a certain extent, since both passive ear protection and constructive measures are able to provide a remedy only to a certain extent. Passive hearing protection measures also have the disadvantage that these are problematic from a hygienic points of view and require the use of disposal articles.

In addition, a device with active ear protection is described in U.S. Pat. No. 5,427,102. Microphones are provided in the vicinity of the ears of the patient in order to pick up the noise produced by a magnetic resonance tomograph. Loudspeakers output what is known as antisound, which is determined in an electronic unit by the measured noise signals in such a way that the antisound largely compensates for the disturbing noise in the vicinity of the ears of the patient. In this case, the loudspeakers are either located in the immediate vicinity of the patient, or the antisound is led to the patient via acoustic waveguides in the form of tubes or pipes. In the first case, however, persons who are likewise present in order to operate the device and/or treat the patient sense the antisound as additional noise, since the antisound is not designed to match the noise level at the location of the operating/treating person. In the second case, the acoustic waveguides are laid loosely within the magnetic resonance tomograph. If the patient is moved, however, movement of the acoustic waveguides is also required. This is complicated and cumbersome. In addition, the frequency response of such an acoustic waveguide is limited, so that under certain circumstances it does not meet the requirements placed on the transmission of the antisound.

U.S. Pat. No. 5,313,945 also discloses a device for active noise compensation. Once again, acoustic waveguides are used, that can result in similar difficulties as described above.

In the case of the device disclosed by GB 2281970 A, the loudspeaker provided is an earphone with electric feedlines. Because of these feedlines, it is possible for the formation of surface waves to occur, which are hazardous to the patient and/or also distortion of the field from the high-frequency (HF) coils or antennas can occur. The $\lambda/4$ grounding provided for this reason cannot avoid the aforementioned hazards with absolute certainty, however. This is because the critical line wavelength substantially depends on the dielectric of the electric feedline. The exact value of the dielectric—which as a rule changes over time—is determined by many influencing variables. For example, the existing air space, the distance from the patient and also movements of the patient play a part.

EP 597528 A1 also describes a device for active noise compensation, in which headphones or loudspeakers, in particular with electric feedlines, are used. The question therefore arises again as to how the aforementioned hazardous surface waves and distortions of the HF field can be avoided.

SUMMARY OF THE INVENTION

One aspect of the invention is, then, based on the object of specifying a method for local reduction of the operating noise produced by a medical diagnostic or therapy device which, with high effectiveness, is technically uncomplicated and hygienically harmless. In addition, one aspect of the invention is based on the object of specifying a medical diagnostic or therapy device which comprises a device that operates in accordance with this method.

According to one aspect of the invention, antisound (an audible noise cancellation sound) is produced locally by a sound source. It is therefore possible to limit the sound level effectively where it develops its disturbing effect. This is possible in particular in the case of diagnostic and therapy devices in which the patient or else the operator is generally located in fixed positions during the diagnostic or therapy procedure, for example in the interior of a magnetic resonance tomography or a lithotripter or at an appropriate operating device. The disturbing noise can then be extinguished in a targeted manner in the vicinity of the head or ear of the patient or of the operator.

The sound source used is preferably a parametric loudspeaker. In a parametric loudspeaker a modulated, inaudible ultrasound signal is produced and the nonlinearity of the acoustic characteristics of air are utilized. Because of this nonlinearity, the air acts as a demodulator, the demodulated signal being present as audible sound. Since ultrasound waves are used as a carrier for the audible sound and can be emitted with a relatively small opening angle in the range of a few degrees of arc, the antisound can be produced in a locally limited manner and specifically at the point where the operating noise disturbs the relevant person, that is to say is perceived by the latter. In particular, the opening angle is at most 15°, preferably at most 5°. The functioning of such a highly directive loudspeaker is explained in more detail, for example, on the Internet page www.atcsd.com/tl_hss/html, as at Jan. 15, 2002, from the American Technology Corporation. Because of the intensive directional action, only the patient perceives the antisound intended for him, while the operator is located outside the closely limited region ensonified by the parametric loudspeaker. The operator then does not perceive the antisound as additional noise which increases the overall noise level, as opposed to the related art. If a parametric loudspeaker is used, there is additionally no direct contact between the patient and the sound source or another part used for the acoustic transmission. Therefore, no specific hygienic measures have to be taken either for the sound source.

Because of the intensive directional action, the parametric loudspeaker can also readily be arranged outside the actual diagnostic and therapy device, that is to say in particular even outside a magnetic resonance tomograph, and can be aligned with its main radiation direction into the interior of the device. No feedline, be it in electric or acoustic form, is then required. The antisound nevertheless gets into the region of the patient's ears because of the directional action.

In this case, the parametric loudspeaker provided is in particular an ultrasonic transducer arrangement constructed from a large number of ultrasonic transducers.

BRIEF DESCRIPTION OF THE DRAWINGS

These and other objects and advantages of the present invention will become more apparent and more readily appreciated from the following description of the preferred embodiments, taken in conjunction with the accompanying drawings of which.

Mutually corresponding parts are provided with the same designations in FIGS. 1 and 2.

DETAILED DESCRIPTION OF THE PREFERRED EMBODIMENT

Figure 1:
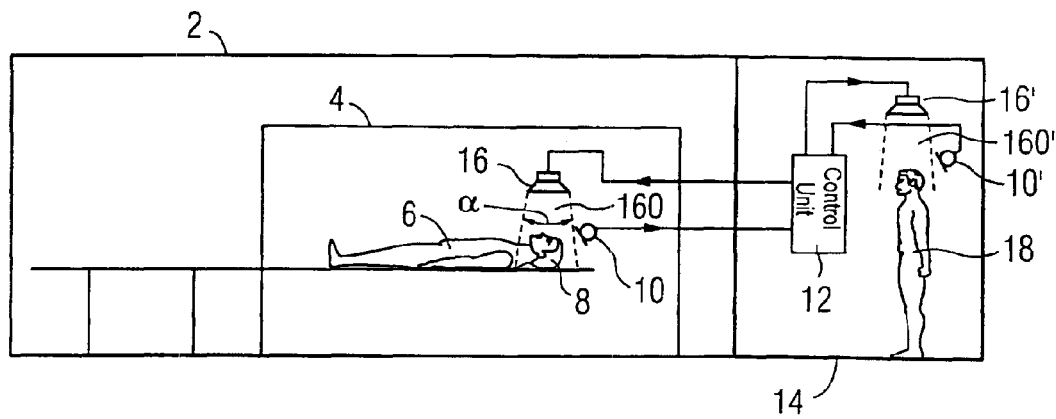
FIG. 1 shows a first medical diagnostic or therapy device in a basic illustration.

Reference will now be made in detail to the preferred embodiments of the present invention, examples of which are illustrated in the accompanying drawings, wherein like reference numerals refer to like elements throughout.

According to FIG. 1, a medical diagnostic or therapy device 4 is arranged in a treatment room 2, in the exemplary embodiment a magnetic resonance tomograph which is illustrated symbolically and in which there is a patient 6.

Arranged in the vicinity of the head 8 of the patient 6 is a sound pickup 10, for example a microphone, which picks up the operating noise occurring in the vicinity of the head and produced by the diagnostic or therapy device 4 and passes it on to an open-loop and closed-loop control unit 12, which is located in an operating cubicle 14. The electric signal passed on to the open-loop and closed-loop control unit 12 by the sound pickup 10 is converted there into a control signal for a sound source 16. The sound source 16 to which the control signal is applied produces what is known as antisound locally in the vicinity of the sound pickup 10 and the head 8. Here, antisound is to be understood to mean a sound field 160 which has approximately the same spectral composition and amplitude as the sound field generated by the diagnostic or therapy device 4. However, as compared with the sound field picked up by the sound pickup 10, the sound field 160 is phase shifted in such a way that the sound field produced by the diagnostic or therapy device 4 and the sound field 160 produced (indirectly) by the sound source 16 at least approximately compensate for each other.

The sound field 160 is produced only indirectly, since the sound source 16 illustrated only symbolically is designed as a highly directional parametric loudspeaker. The parametric loudspeaker directly produces an ultrasound signal that cannot be perceived by the human ear. The signal is modulated in such a way that the nonlinear acoustic characteristics of the propagation medium, that is to say the air here, act as a demodulator. The demodulated signal which results is then an audible sound signal, here the antisound used for active sound compensation. The fact that the sound source produces an ultrasound signal directly means that a very intensive directional action can be set, even for the audible antisound produced only indirectly. An opening angle $\alpha$ of the sound lobe is very small and, in particular, lies between 1° and 5°, 3° in the example of FIG. 1. The opening angle $\alpha$ is in this case defined as the angular range within which the sound pressure level is at at least 50% of the maximum sound pressure (=−3 dB limit). The opening angle $\alpha$ is also indicated in the illustration of FIG. 1.

The parametric loudspeaker of the sound source 16 comprises a two-dimensional flat arrangement comprising a large number of, in particular, piezoelectric polyvinylidene fluoride PVDF ultrasonic transducers. As distinct from a magnetic sound source, a piezoelectric sound source is very compatible with MR, that is to say is suitable for use at the high magnetic field strengths which are present in the interior and to some extent also in the outer space of a magnetic resonance tomograph.

Figure 2:
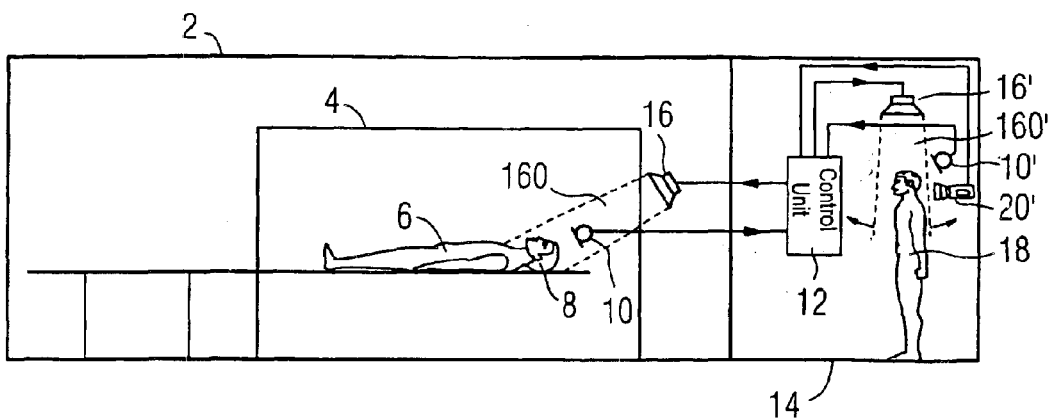
FIG. 2 shows a second medical diagnostic or therapy device, likewise in a basic illustration.

The use of a highly directional loudspeaker 16 makes it possible even to arrange the latter outside the magnetic resonance tomograph and to direct the sound produced by it specifically through an opening which is preferably present in any case in a tomograph magnet onto the head 8 of the patient 6 (see FIG. 2). The parametric loudspeaker can, however, also be located inside the magnetic resonance tomograph (see FIG. 1). For example, integration into the lining of a tomograph magnet is possible.

In principle, the use of a plurality of sound pickups 10 and sound sources 16 in each case assigned to the latter is also possible. For example, a sound pickup 10 can be arranged in the vicinity of each ear of the patient 6.

In addition, a sound pickup 10' and sound sources 16' can also be provided in the operating cubicle 14, in order likewise to protect the operator 18 from an excessively high noise loading. In this case, acoustic contact, that is to say a bidirectional communication channel, between patient 6 and operator 18 is additionally possible without difficulty. It is substantially possible in this case to have recourse to the components needed in any case for active sound compensation. The sound pickups 10 and 10' and also the sound sources 16 and 16' at the patient 6 and at the operator 18 can also be used for the bidirectional communication. In the case where known sound sources are used with a small or even no directional action, such a communications channel may possibly be set up only under very much greater difficulties, since disturbing overlapping occurs between the sound fields produced by the nondirectional sound sources.

Furthermore, another signal, for example a music signal, can also be superimposed on the control signal for the antisound. Then, not only is the disturbing operating noise of the magnetic resonance tomograph largely kept away from the patient, but the latter can additionally also hear music. As a result, the examination/treatment in the magnetic resonance tomograph, which is narrow and also very loud without sound compensation, can be configured to be considerably more pleasant for the patient.

In the device shown in FIG. 2, a registration device for registering the (head) position of the operator 18 is also provided. In the example, a camera 20' is used as registration device. The camera 20' is connected to the open-loop and closed-loop control unit 12. The picture information picked up by the camera 20' is used there to track the sound field 160' produced by the sound source 16' to the current position of the operator 18 (=target antisound region). For this purpose, the direction of the sound field 160' can be adjusted, as indicated schematically in FIG. 2. Appropriate mechanical or electronic adjusting unit are provided. Particularly beneficial is electronic adjustment, which may be achieved in a simple way by variable electronic activation of the individual PVDF ultrasonic transducers of the parametric loudspeaker 16 (=the functioning of what is known as a phased array). The activation varied in this way can also be carried out by the open-loop and closed-loop control unit 12, which is present in any case. The possibility of changing the radiation direction is advantageous in particular when a highly directional parametric loudspeaker is used. This is because it is thereby possible to ensure that the antisound from the sound field 160' reaches the operator 18 even when the latter moves, in particular when he leaves the region originally covered by the sound field 160'. Although not explicitly illustrated in FIG. 2, such a possible adjustment of the radiation direction can also be provided if required, for the sound source 16 covering the patient 6.

The measures for active sound compensation, described above using the example of a magnetic resonance tomograph, are not restricted to this device type. Rather, they can also be used in the same or similar way to compensate for disturbing operating noise from other medical diagnostic or therapy devices.

The invention has been described in detail with particular reference to preferred embodiments thereof and examples, but it will be understood that variations and modifications can be effected within the spirit and scope of the invention.

What is claimed is:

1. A method for local reduction of operating noise comprising:
   producing an audible noise cancellation sound locally by a sound source in an area of operating noise produced by a medical diagnostic or therapy device, the sound source being an ultrasonic transducer highly directional parametric loudspeaker; and
   directing the noise cancellation sound toward the head of a patient on which the medical diagnostic or therapy device is being used,
   wherein the noise cancellation sound is produced based on nonlinear acoustic characteristics of a transmission medium between the sound source and the patient.

2. The method as claimed in claim 1, wherein the noise cancellation sound is radiated within an opening angle of less than 15°.

3. The method as claimed in claim 1, wherein the noise cancellation sound is radiated within an opening angle of less than 5°.

4. The method as claimed in claim 3, wherein a target region of the noise cancellation sound is monitored for a position change.

5. The method as claimed in claim 4, further comprising varying a radiation direction of the noise cancellation sound as a function of the position change in the target region.

6. The method as claimed in claim 1, wherein a target region of the noise cancellation sound is monitored for a position change.

7. The method as claimed in claim 6, further comprising varying a radiation direction of the noise cancellation sound as a function of the position change in the target region.

8. A medical diagnostic or therapy device comprising:
   a device to generate a diagnostic or therapy signal and an undesirable audible signal;
   a sound source which is an ultrasonic transducer highly directional parametric loud speaker;
   a control unit;
   a sound pickup connected via the control unit to the sound source, the sound source indirectly producing an audible noise cancellation sound directed toward the head of a patient to reduce a noise level of the undesirable audible signal at least in an environment of the sound pickup.

9. The medical diagnostic or therapy device as claimed in claim 8, wherein ultrasonic transducer is made of polyvinylidene fluoride.

10. The medical diagnostic or therapy device as claimed in claim 9, wherein the sound source has an opening angle of less than 5°.

11. The medical diagnostic or therapy device as claimed in claim 10, further comprising a registration device to register a position change of a target noise cancellation sound region.

12. The medical diagnostic or therapy device as claimed in claim 11, further comprising an adjusting unit to adjust a radiation direction for the noise cancellation sound as a function of the position change of the target noise cancellation sound region.

13. The medical diagnostic or therapy device as claimed in claim 9, wherein
   the device is a magnetic resonance tomograph having a magnetic field strength, and
   the ultrasonic transducer is exposed to the high magnetic field strength.

14. The medical diagnostic or therapy device as claimed in claim 8, wherein the sound source has an opening angle of less than 15°.

15. The medical diagnostic or therapy device as claimed in claim 8, wherein the sound source has an opening angle of less than 5°.

16. The medical diagnostic or therapy device as claimed in claim 8, further comprising a registration device to register a position change of a target noise cancellation sound region.

17. The medical diagnostic or therapy device as claimed in claim 16, further comprising an adjusting unit to adjust a radiation direction for the noise cancellation sound as a function of the position change of the target noise cancellation sound region.

18. The medical diagnostic or therapy device as claimed in claim 8, wherein the control unit is an open-loop and closed-loop control unit.

19. The medical diagnostic or therapy device as claimed in claim 8, further comprising super-imposing another signal on the noise cancellation sound.

20. The medical diagnostic or therapy device as claimed in claim 19, wherein the other signal is music.

21. A medical diagnostic or therapy device comprising:
   a device to generate a diagnostic or therapy signal and an undesirable audible signal, the device being operated by an operator;
   a sound source which is an ultrasonic transducer highly directional parametric loud speaker, the sound source indirectly producing an audible noise cancellation sound directed toward the head of the operator;
   a sound pickup positioned in the vicinity of the head of the operator; and
   a control unit receiving feedback from the sound pickup to control the sound source to reduce a noise level of the undesirable audible signal at least in a vicinity of the sound pickup and the head of the operator.

* * * * *